US008977530B2

(12) United States Patent
Lee et al.

(10) Patent No.: US 8,977,530 B2
(45) Date of Patent: Mar. 10, 2015

(54) METHOD FOR IDENTIFYING GENES FOR ENHANCING THE PRODUCTION OF USEFUL SUBSTANCES

(75) Inventors: Sang Yup Lee, Daejeon (KR); Han Min Woo, Ul-san (KR); Hyung Seok Choi, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 1194 days.

(21) Appl. No.: 11/722,709

(22) PCT Filed: Sep. 15, 2005

(86) PCT No.: PCT/KR2005/003074
§ 371 (c)(1),
(2), (4) Date: Mar. 24, 2008

(87) PCT Pub. No.: WO2007/032568
PCT Pub. Date: Mar. 22, 2007

(65) Prior Publication Data
US 2008/0220490 A1 Sep. 11, 2008

(51) Int. Cl.
*G06G 7/48* (2006.01)
*G06F 19/12* (2011.01)

(52) U.S. Cl.
CPC .................................. *G06F 19/12* (2013.01)
USPC .......................................................... 703/11

(58) Field of Classification Search
None
See application file for complete search history.

(56) References Cited

U.S. PATENT DOCUMENTS

| | | | |
|---|---|---|---|
| 6,159,738 A | 12/2000 | Donnelly et al. | |
| 7,127,379 B2 | 10/2006 | Palsson et al. | |
| 7,711,490 B2 * | 5/2010 | Maranas et al. | 702/19 |
| 2002/0168654 A1 | 11/2002 | Maranas et al. | |
| 2003/0059792 A1 | 3/2003 | Palsson et al. | |
| 2004/0009466 A1 | 1/2004 | Maranas et al. | |
| 2006/0162020 A1 * | 7/2006 | Sauer et al. | 800/282 |
| 2009/0075352 A1 | 3/2009 | Lee et al. | |

FOREIGN PATENT DOCUMENTS

| | | |
|---|---|---|
| JP | 2005-058226 A | 3/2005 |
| JP | 2005-293394 A | 10/2005 |
| JP | 2008-527991 A | 7/2008 |
| JP | 2009-535055 A | 10/2009 |
| KR | 10-0655495 B1 | 12/2006 |
| WO | 2007007933 A1 | 1/2007 |

OTHER PUBLICATIONS

Edwards et al. (Nature Biotechnology, 2001, 19, 125-130).*
Berry et al. (Journal of Industrial Microbiology & Biotechnology, 2002, 28, 127-133).*
Edwards, Robert A., et al., "A role for *Salmonella* fimbriae in intraperitoneal infections", "Proc. Natl. Acad. Sci. USA", Feb. 1, 2000, pp. 1258-1262, vol. 97, No. 3.
Forster, Jochen, et al., "Genome-Scale Reconstruction of the *Saccharomyces cerevisiae* Metabolic Network", "Genome Res.", Feb. 2003, pp. 244-253, vol. 13, No. 2.
Lee, Sang Yup, et al., "Systems biotechnology for strain improvement (Abstract Only)", "Trends Biotechnol.", Jul. 2005, pp. 349-358, vol. 23, No. 7.
Pharkya, Priti, et al., "Exploring the overproduction of amino acids using the bilevel optimization framework OptKnock", "Biotechnol. Bioeng.", Dec. 30, 2003, pp. 887-899, vol. 84, No. 7.
Segre, Daniel, et al., "Analysis of optimality in natural and perturbed metabolic networks", "Proc. Natl. Acad. Sci. USA", Nov. 12, 2002, pp. 15112-15117, vol. 99, No. 23.
Alper, Hal, et al., "Identifying gene targets for the metabolic engineering of lycopene biosynthesis in *Escherichia coli*", "Metab. Eng.", May 2005, pp. 155-164, vol. 7, No. 3.
Burgard, Anthony P., et al., "Optknock: A bilevel programming framework for identifying gene knockout strategies for microbial strain optimization", "Biotechnol. Bioeng.", Dec. 20, 2003, pp. 647-657, vol. 84, No. 6.
Farmer, William R., et al., "Improving lycopene production in *Escherichia coli* by engineering metabolic control", "Nat. Biotechnol.", May 2000, pp. 533-537, vol. 18, No. 5.
Varma, Amit, et al., "Metabolic Capabilities of *Escherichia coli* II. Optimal Growth Patterns", "J. Theor. Biol.", Dec. 21, 1993, pp. 503-522, vol. 165, No. 4.
Stephanopoulos, et al., "Metabolic Flux Analysis", "Metabolic Engineering", 1998, p. 309, Publisher: Academic Press, Published in: New York, NY.
Choi, H. et al., "In Silico Identification of Gene Amplification Targets for Improvement of Lycopene Production", "Applied and Environmental Microbiology", May 2010, pp. 3097-3105, vol. 76, No. 10.
Hong, Soon Ho, et al., "In silico prediction and validation of the importance of the Entner-Doudoroff pathway in poly(3-hydroxybutyrate) . . . ", "Biotechnol. Bioeng.", Sep. 30, 2003, pp. 854-863, vol. 83, No. 7.
Hong, S.H., et al., "Enhanced production of succinic acid by metabolically engineered *Escherichia coli* with amplified activities of malic . . . ", "Biotechnol. Bioprocess Eng.", 2004, pp. 252-255, vol. 9.
Hou, Bo Kyeng, et al., "BioSilico: an integrated metabolic database system", "Bioinform.", Nov. 22, 2004, pp. 3270-3272, vol. 20, No. 17.

(Continued)

*Primary Examiner* — Pablo S Whaley
(74) *Attorney, Agent, or Firm* — Hultquist, PLLC; Steven J. Hultquist

(57) ABSTRACT

Provided is a method for improving useful substance-producing organisms using metabolic flux analysis, and more particularly a method for improving a host organism producing a useful substance, the method including: calculating a maximum flux value corresponding to the theoretical maximum yield of the useful substance in the metabolic network model of the host organism for producing useful substance, and calculating the optimum value of metabolic flux associated with useful substance production in the metabolic network when the value of cell growth-associated metabolic flux is the maximum under the condition where fermentation data are applied or not applied; selecting metabolic fluxes whose absolute values increase from the range between the maximum value and the optimum value; screening genes associated with the selected metabolic fluxes; and introducing and/or amplifying the selected genes in the host organism. Production of the useful substance can be effectively improved by using the method.

5 Claims, 5 Drawing Sheets

(56) References Cited

OTHER PUBLICATIONS

Kim, Do Yun, et al., "Batch and continuous fermentation of succinic acid from wood hydrolysate by *Mannheimia succiniciproducens* MBEL55E", "Enzyme Microb. Technol.", Dec. 1, 2004, pp. 648-653, vol. 35, No. 6-7.

Nam, Jae Wook, et al., "In silico analysis of lactate producing metabolic network in *Lactococcus lactis*", "Enzyme Microb. Technol.", Dec. 1, 2004, pp. 654-662, vol. 35, No. 6-7.

Varma, Amit, et al., "Metabolic Flux Balancing: Basic Concepts, Scientific and Practical Use", "Bio/Technol.", Oct. 1994, p. 994, vol. 12, No. 10.

\* cited by examiner

METHOD FOR IDENTIFYING GENES FOR ENHANCING THE PRODUCTION OF USEFUL SUBSTANCES

CROSS-REFERENCE TO RELATED APPLICATION

This application is filed under the provisions of 35 USC §371 and claims the benefit of priority of International Patent Application No. PCT/KR2005/003074, filed 15 Sep. 2005. The disclosure of said application is hereby incorporated herein by reference in its entirety.

TECHNICAL FIELD

The present invention relates to a method for improving useful substance-producing organisms using metabolic flux analysis, and more particularly, to a method for improving a host organism producing a useful substance, the method comprising: calculating a maximum flux value corresponding to the theoretical maximum yield of the useful substance in the metabolic network model of the host organism for producing a useful substance, and calculating the optimum value of metabolic flux associated with useful substance production in the metabolic network, when the value of cell growth-associated metabolic flux is the maximum under the condition where fermentation data are applied or not applied; selecting metabolic fluxes whose absolute values increase in the range between the maximum value and the optimum value; screening genes associated with the selected metabolic fluxes; and introducing and/or amplifying the selected genes in the host organism.

BACKGROUND ART

In the prior art, there have been many attempts to improve producer strains and increase target metabolites using metabolic engineering approaches. However, the prior metabolic engineering methods for improving strains using molecular biological techniques required much higher cost and effort based on trial-and-error strategy. Recently, with the accumulation of genomic information and the development of various high-throughput screening techniques, methods capable of maximizing the production of useful substances in strains improved by metabolic engineering have been being developed. Particularly, as the entire genome sequences of various useful microorganisms have been identified, the construction of metabolic network models has become possible, thereby making substantial studies possible.

Thus, the use of the previously constructed metabolic network models made metabolic flux analysis possible under the assumption that "microorganisms undergo metabolic processes for the growth thereof (Varma et al., *J. Theor. Biol.*, 165:503, 1993). As a result, the metabolic flux analysis can effectively provide the following, for example: (1) the identification of branch points in metabolic pathways; (2) the identification of substitute pathways; (3) the calculation of unmeasured external metabolites; and (4) the calculation of maximum theoretical yield (Stephanopoulos et al., Metabolic Engineering, Academic Press, NY, 309, 1998).

On the basis of the understanding of a huge amount of information provided recently, the development of new techniques for the development of effective producer strains is actively ongoing. By acquiring of the genome information of useful microorganisms by high-throughput screening techniques, metabolic network models were constructed (Edwards et al., *Proc. Natl. Acad. Sci.*, 13:244, 2000; Foster et al., *Genome Res.*, 13:244, 2003). Also, metabolic flux analysis methods for investigating integrated metabolic functions on the basis of metabolic network models were developed (Varma et al., *J. Theor. Biol.*, 165:503, 2003; US 2002/0168654 A1). On the basis of these analysis methods, techniques capable of screening genes to be deleted based on metabolic network models so as to increase useful products of producer strains were developed. The Optknock method comprising screening genes to be deleted through the optimization of two axes consisting of flux for production and flux for growth and optimizing objective functions different from each other (Burgard et al., *Biotechnol. Bioeng.*, 84:647, 2002, US 2004/0009466 A1), and the MOMA (minimization of metabolic adjustment) method capable of obtaining a partial optimal point by minimizing the migration of the optimum point caused by primary gene deletion of a strain having deletion of candidate gene from a wild-type strain was developed (Segre et al., *Proc. Natl. Acad. Sci.*, 99:15112, 2002). On the basis of these methods, a gene screening method capable of screening genes to be sequentially deleted the first time, the second time and the third time was developed and actually applied for the production of lycopene (Alper et al., *Metab. Eng.*, 7:155, 2004). In addition, a method for screening key metabolites increasing production yield of useful substances, comprising defining the metabolite utilization of a useful substance-producing organism as flux sum and perturbing the defined flux sum, and a method for improving a useful substance-producing organism by deleting and/or amplifying genes associated with said screened key metabolites were developed and applied for patent protection (Korean Patent Application No. 10-2005-62404).

In metabolic flux analysis, flux for production and flux for cell growth are generally in inverse proportion to each other (see FIG. 1). This indicates that, in the case of common microorganisms, the production of useful substances inhibits the growth of cells. For this reason, methods for increasing the production of useful substances through appropriate metabolic engineering techniques are required. Typical molecular biological approaches for achieving the metabolic engineering purpose include gene amplification techniques inducing the overexpression of target genes. Accordingly, for the improvement of organisms to improve the production of useful substances, the introduction of techniques for systematically amplifying genes and the development of techniques for applying the genes to organisms have recently been required in the field of art.

DISCLOSURE OF THE INVENTION

The present inventors have found that a host organism producing a useful substance can be improved by a method comprising: calculating a maximum flux value corresponding to the theoretical maximum yield of the useful substance in the metabolic network model of the host organism for producing a useful substance, and calculating the optimum value of metabolic flux associated with useful substance production in the metabolic network model, when the value of cell growth-associated metabolic flux is the maximum under the condition where fermentation data are applied or not applied; selecting metabolic fluxes whose absolute values increase in the range between the maximum value and the optimum value; screening genes associated with the selected metabolic fluxes; and introducing and/or amplifying the selected genes in the host organism. On the basis of this finding, the present invention has been completed.

It is therefore an object of the present invention to provide a method for screening genes to be amplified for enhancing the production of a useful substance.

Another object of the present invention is to provide a method for improving a useful substance-producing host organism by introducing an/or amplifying said screened genes in the host organism.

To achieve the above objects, in one aspect, the present invention provides a method for screening genes to be amplified for enhancing the production of a useful substance, the method comprising the steps of: (a) selecting a host organism (except for human beings) for producing the useful substance, and constructing the metabolic network model of the selected organism; (b) calculating the maximum value of metabolic flux associated with useful substance production in the constructed metabolic network of the selected organism, which corresponds to the theoretical maximum yield of the useful substance, and calculating the optimum value of metabolic flux associated with useful substance production in the metabolic network, when the value of growth-associated metabolic flux is the maximum under the condition where fermentation data are applied or not applied; (c) executing an FSEOP (flux scanning based on enforced objective flux) algorithm in the range between the maximum and optimum values of metabolic flux calculated in the step (b) so as to construct a profile of all the metabolic fluxes of the metabolic network; (d) screening genes involved in the selected metabolic fluxes as genes to be primarily amplified when absolute maximum values are greater than absolute optimum values among absolute values of the whole metabolic fluxes from the profile constructed in the step (c); and (e) finally selecting genes involved in metabolic fluxes showing monotonous increase or decrease from the genes to be primarily amplified, which is screened in the step (d) as genes to be finally amplified.

In another aspect, the present invention provides a method for improving an organism producing a useful substance, the method comprising the steps of: (a) selecting a host organism (except for human beings) for producing the useful substance, and constructing the metabolic network model of the selected organism; (b) calculating the maximum value of metabolic flux associated with useful substance production in the constructed metabolic network of the selected organism, which corresponds to the theoretical maximum yield of the useful substance, and calculating the optimum value of metabolic flux associated with useful substance production in the metabolic network, when the value of growth-associated metabolic flux is the maximum under the condition where fermentation data are applied or not applied; (c) executing an FSEOP (flux scanning based on enforced objective flux) algorithm in the range between the maximum and optimum values of metabolic flux calculated in the step (b) so as to construct a profile of all the metabolic fluxes of the metabolic network; (d) screening genes involved in the selected metabolic fluxes as genes to be primarily amplified when absolute maximum values are greater than absolute optimum values among absolute values of the whole metabolic fluxes from the profile constructed in the step (c); and (e) finally selecting genes involved in metabolic fluxes showing monotonous increase or decrease from the genes to be primarily amplified, which is screened in the step (d) as genes to be finally amplified; and (f) introducing the genes finally selected in the step (e) into the host organism and/or amplifying the finally selected genes in the host organisms, so as to construct a mutant of the host organism.

Preferably, the inventive method for improving the host organism may additionally comprise the step (g) of culturing the mutant organism constructed in the step (f) so as to experimentally examine the production of the useful substance.

In the present invention, the host organism is preferably a microorganism, and the useful substance is preferably any one selected from the group consisting of metabolites having high industrial utility, which includes lycopene, shikimate and indigo. Also, the host organism is preferably a microorganism having the ability to produce a useful substance selected from the group consisting of metabolites having high industrial utility, which includes lycopene, shikimate and indigo.

In the present invention, the genes to be amplified for producing lycopene are preferably selected from the group consisting of fbaA, tpiA, mdh and idi, the genes to be amplified for producing shikimate are preferably selected from the group consisting of glk, pgi, tktA, talA, talB and aroG, and the genes to be amplified for producing indigo are preferably selected from the group consisting of pgi, glk, fbaA, ppsA, tktA, rpiA and aceB.

In the step (b) of the inventive method, the optimum value of useful substance production-associated metabolic flux, when the value of growth-associated metabolic flux is the maximum under the condition where fermentation data are applied or not applied, is preferably calculated using the following algorithm:

$$v_{Biomass\ objective} \quad \text{maximization}$$

$$\sum_{j=1}^{M} S_{ij} v_j = 0 \quad \forall\, i \in M, \forall\, j \in N$$

$$v_j^\alpha \leq v_j \leq v_j^\beta \qquad v_j \in i$$

Also, in the step (b), the maximum value corresponding to the theoretical maximum yield of the useful substance production-associated metabolic flux is preferably calculated using the following algorithm:

$$v_{product\ objective} \quad \text{maximization}$$

$$\sum_{j=1}^{M} S_{ij} v_j = 0 \quad \forall\, i \in M, \forall\, j \in N$$

$$v_j^\alpha \leq v_j \leq v_j^\beta \qquad v_j \in i$$

Also, the FSEOF algorithm in the step (c) is preferably represented as follows:

$$v_{Biomass\ objective} \quad \text{maximization}$$

$$f_{p,j} = f_{p,opt} + \frac{y_k}{n}(f_{p,max} - f_{p,opt})$$

$$Y = \{y_k \in \mathcal{C} \mid y_k = 0, 1, \ldots, n\}$$

$$\left[ \begin{array}{l} \sum_{j=1}^{M} S_{ij} v_j = 0 \quad \forall\, i \in M, \forall\, j \in N \\ v_j^\alpha \leq v_j \leq v_j^\beta, \qquad v_j \in R \end{array} \right]$$

$$\text{if } |v_j|_{max} > |v_{opt}|, v_j \text{ is selected,}$$

wherein S is the reaction coefficient matrix of the metabolic network, $v_j$ is metabolic flux, $v_{opt}$ is the optimum value of metabolic flux, $|v_j|_{max}$ is the absolute maximum value of metabolic flux, calculated by the FSEOF algorithm, $f_{p,i}$ is production-associated metabolic flux, $f_{p,max}$ is the maximum value corresponding to the theoretical maximum yield of production-associated metabolic flux, $f_{p,opt}$ is the optimum value of useful substance production-associated metabolic flux, when the value of growth-associated metabolic flux is the maximum under the condition where fermentation data are applied or not applied, Y is a set including the characteristic factor of the step procedure of the FSEOF algorithm, and $y_k$ is the characteristic factor of the step procedure of the FSEOF algorithm in the set Y.

In the present invention, if the metabolic network model in the step (a) is not specific for the production of the target useful substance, a metabolic network for the production of the useful substance can be additionally used to construct the metabolic network model.

In another aspect, the present invention provides a method for preparing a useful substance, the method comprises culturing the organism improved according to the above improvement method.

In still another aspect, the present invention provides a mutant strain in which a gene selected from the group consisting of fbaA, tpiA, mdh and idi has been introduced and/or amplified and which has the ability to produce a high quantity of lycopene. Also, the present invention provides a mutant E. coli strain in which a gene selected from the group consisting of fbaA, tpiA, mdh and idi has been introduced and/or amplified.

In still another aspect, the present invention provides a method for producing lycopene, the method comprises culturing said mutant strain or mutant E. coli strain in an aerobic conditions.

Other features and embodiments of the present invention will be more clearly understood from the following detailed description and the appended claims.

DETAILED DESCRIPTION OF THE INVENTION, AND PREFERRED EMBODIMENTS THEREOF

Hereinafter, the present invention will be described in detail. In the present invention, the genes to be amplified are screened through the FSEOF algorithm that selects metabolic fluxes whose absolute values increase, in the range between the optimum value and maximum value of metabolic flux associated with useful substance production.

The screened genes to be amplified may be introduced into a useful substance-producing organism by an expression vector and/or amplified in the organism so as to increase relevant metabolic fluxes in the organism, thus maximizing the production of the target useful substance.

To execute an algorithm for screening genes to be amplified, a metabolic network model must be first constructed. In the present invention, if the metabolic network model of the host organism is not specific for the production of the target useful substance, a metabolic flux for the production of the target useful substance was additionally used to construct the metabolic network model in order to make a metabolic network model more suitable for the production of the target useful substance.

Figure 1:
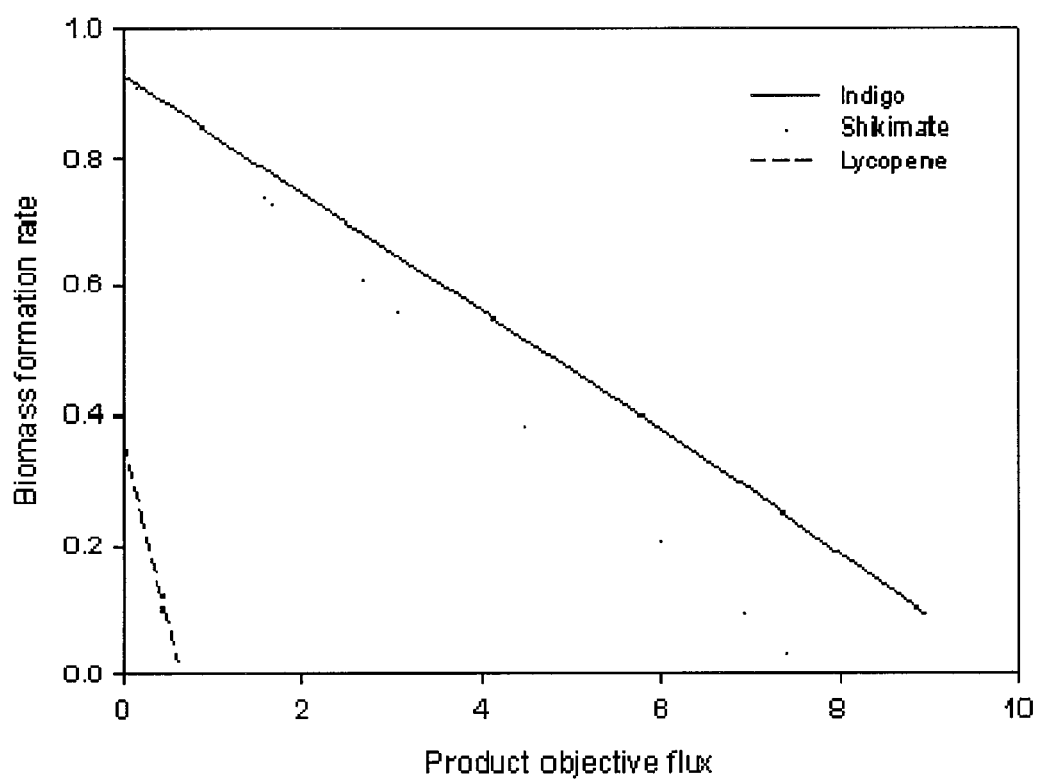
FIG. 1 shows the relationship between metabolic flux for production and metabolic flux for cell growth.
Figure 2:
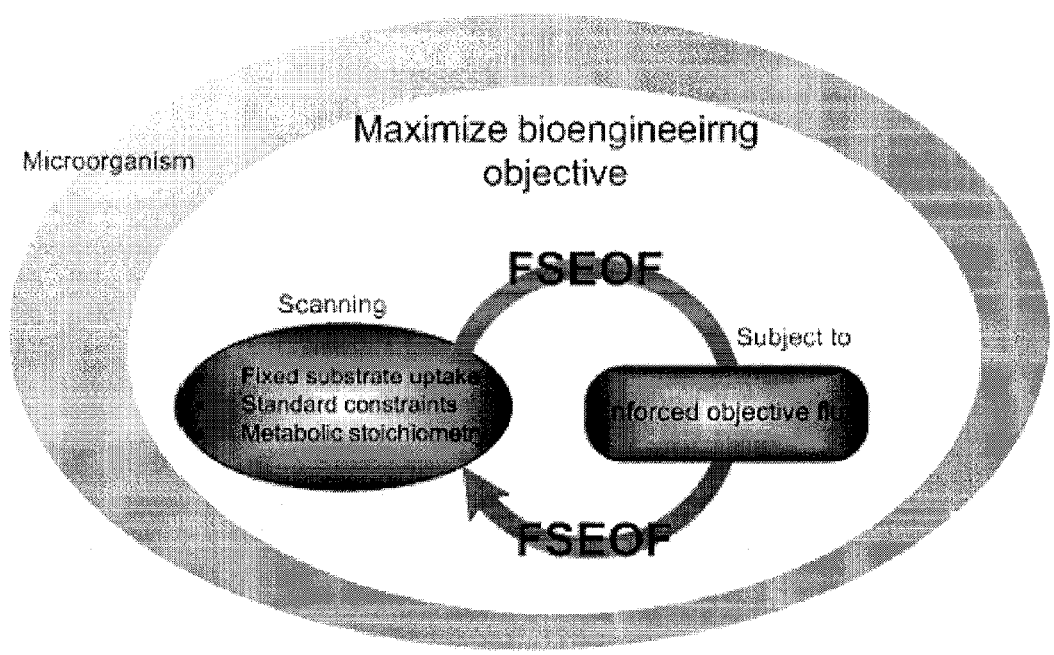
FIG. 2 schematically shows an FSEOF algorithm according to the present invention.

FIG. 2 schematically shows an FSEOF algorithm which is used in the present invention. As shown in FIG. 2, all metabolic fluxes are analyzed while artificially adjusting target useful substance metabolic flux value associated with production. Based on the analyzed metabolic fluxes, metabolic fluxes to be amplified and genes associated therewith are screened. These analysis and screening steps will now be described in detail.

Prior to applying the FSEOF algorithm, the calculation of metabolic flux needs to be performed. By performing metabolic flux analysis for a metabolic network model constructed from a preliminary experiment, the optimum values of all metabolic fluxes, when the values of growth-associated metabolic fluxes in the metabolic network are the maximum, are calculated. These optimal metabolic flux values are recorded as the start points of the FSEOF algorithms. At the same time, the optimal values of production-associated metabolic fluxes are recorded and these values are used as start points for enhancing the values of production-associated metabolic fluxes. The mathematical representation of metabolic flux analysis for calculating the optimal metabolic flux values in the metabolic network is as follows:

$$v_{Biomass\ objective} \quad \text{maximization}$$

$$\sum_{j=1}^{M} S_{ij} v_j = 0 \quad \forall\, i \in M,\ \forall\, j \in N$$

$$v_j^\alpha \leq v_j \leq v_j^\beta \qquad v_j \in i$$

wherein S is a reaction coefficient matrix constituting the metabolic network, the reaction coefficient of a reactant is expressed as a negative number and the reaction coefficient of a product is expressed as a positive number, so that all the reaction coefficients will balance the reaction in an atomic unit. In the calculation of linear equations, previously acquired information (i.e., conditions such as substrate uptake rate and thermodynamic restriction) can be added to obtain more accurate calculated results.

Also, as additional necessary conditions for the FSEOF algorithm, the theoretical maximum yield values of production-associated metabolic fluxes are required. Using metabolic flux analysis for the constructed metabolic flux model together with various restriction conditions, the maximum value (theoretical maximum yield) of production-associated metabolic flux is calculated when the value of production-associated metabolic fluxes is the maximum in the metabolic network. Based on this value, the final value of production-associated metabolic flux to be enforced is calculated. In the similar manner to the above-described mathematical equation for the optimum value, the maximum value (theoretical maximum yield) of production-associated metabolic flux can be calculated using the following mathematical equation:

$v_{product\ objective}$  maximization $$\sum_{j=1}^{M} S_{ij} v_j = 0 \quad \forall i \in M, \forall j \in N$$

$$v_j^\alpha \leq v_j \leq v_j^\beta \qquad v_j \in i$$

As a result of calculation by the mathematical equations, the optimum value and maximum value of production-associated metabolic flux can be obtained, and based on these values, the FSEOF algorithm represented as follows can be applied. By the FSEOF algorithm, metabolic fluxes to be primarily amplified are screened.

$v_{Biomass\ objective}$  maximization $$f_{p,j} = f_{p,opt} + \frac{y_k}{n}(f_{p,max} - f_{p,opt})$$

$$Y = \{y_k \in \not\subset \mid y_k = 0, 1 \ldots, n\}$$

$$\left[\begin{array}{l} \sum_{j=1}^{M} S_{ij} v_j = 0 \quad \forall i \in M, \forall j \in N \\ v_j^\alpha \leq v_j \leq v_j^\beta, \qquad v_j \in R \end{array}\right]$$

if $|v_j|_{max} > |v_{opt}|$, $v_j$ is selected, wherein S is the reaction coefficient matrix of the metabolic network, $v_j$ is metabolic flux, $v_{opt}$ is the optimum value of metabolic flux, $|v_j|_{max}$ is the absolute maximum value of metabolic flux, calculated by the FSEOF algorithm, $f_{p,i}$ is production-associated metabolic flux, $f_{p,max}$ is the maximum value corresponding to the theoretical maximum yield of production-associated metabolic flux, is the optimum value of production-associated metabolic flux of useful substances when the value of growth-associated metabolic flux is the maximum in a condition where fermentation data are applied or not applied, Y is a set including the characteristic factor of the step procedure of the FSEOF algorithm, and $y_k$ is the characteristic factor of the step procedure of the FSEOF algorithm in the set Y.

The range between the optimum value and maximum value of production-associated metabolic flux is divided into several sections, and metabolic flux value is increased in the same section interval while constructing a linear equation so as to be restricted to that value. Based on the model thus constructed, metabolic flux value at which cell growth rate is the maximum is calculated repetitively. To calculate the metabolic flux, the following software programs can be used: Matlab-based software programs such as FluxAnalyzer (Klamt et al., Bioinformatics, 19:216, 2003) and Metabologica (Zhu et al., Metab. Eng., 5:74, 2003), software programs allowing independent calculation, such as Fluxor, Simpheny (Genomatica Inc., San Diego, Calif.), INSILICO Discovery (INSILCO biotechnology Inc., Stuttgart, Germany), FBA, and MetaFluxNet (Lee et al., Bioinformatics, 19:2144, 2003), Gams (GAMS Development Corporation, NW Washington, D.C.), and computer language package tools, such as C language or Fortran.

From the result of the repeated calculation, among the absolute values of all the metabolic fluxes, those having an absolute maximum value greater than absolute optimum value, i.e., metabolic fluxes having a necessarily increasing section, are primarily screened as metabolic fluxes to be amplified.

Then, through metabolic flux analysis for the primarily screened metabolic fluxes, metabolic fluxes to be ultimately amplified and genes to be amplified, which is involved in these metabolic fluxes, are finally screened. In the final screening, among the primarily screened metabolic fluxes, those showing a tendency to decrease or increase but having an absolute maximum value greater than absolute optimum value only in a few sections were excluded.

The patterns of the metabolic fluxes screened according to the above-described method showed the form of monotonous increase or decrease. The optimum value of a positive number means a value continuously increasing in the forward direction, and the optimum value of a negative number means a value increasing in the reverse direction. Also, as the left and right positions of reactants and products change, a monotonous decrease in a negative number was shown.

However, since the metabolic fluxes primarily screened through the FSEOF algorithm result from the process of screening sections showing an increase in the change of absolute value, it can be considered that the primarily screened metabolic fluxes are regardless of a positive number or negative number of the optimum value. For this reason, those swung or not started from a value of zero are also screened as metabolic fluxes to be amplified. Accordingly, among these metabolic flux patterns, metabolic fluxes which do not increase in a consistent pattern or which change from a forward direction to a reverse direction or vice versa in the metabolic network were excluded from metabolic fluxes to be ultimately amplified.

Namely, in the inventive process for screening genes to be amplified, among genes associated with all metabolic fluxes, genes to be amplified were primarily screened through the FSEOF algorithm, and among the primarily screened genes, genes to be ultimately amplified were screened by analyzing metabolic flux profiles.

The inventive method for screening genes to be amplified can be applied for the overproduction of a target useful substance. In the following examples, in order to verify the utility of the FSEOF algorithm, the production of each of lycopene, shikimate and indigo in *E. coli* was actually performed and literature review was carried out. As a result, it could be proved that the amplification of genes screened using the FSEOF algorithm contributed to an increase in the production of a target metabolic substance.

EXAMPLES

Hereinafter, the present invention will be described in more detail by examples. It is to be understood, however, that these examples are for illustrative purpose only and are not construed to limit the scope of the present invention.

Particularly, although the following examples illustrate lycopene, shikimate and indigo as useful substances, a person skilled in the art will appreciate that any useful substance can be applied as long as it can be produced through the culture of organisms.

Example 1

Screening of Genes to be Amplified, which Increase the Production of Lycopene

Lycopene, as a secondary metabolite, is a $C_{40}$ carotenoid compound that acts as antioxidant by blocking active oxygen, helps to prevent cancer, and plays an important role in enhancing the immune system. Carotenoid compounds are mainly obtained by extraction from plants, and there is a significant difficulty in sufficiently producing various derivatives of lycopene. The production of lycopene in bacteria introduced with foreign genes shows good efficiency and allows to obtain various derivatives of lycopene to be obtained through genetic manipulation. Thus, the overproduction of lycopene can lead to the overproduction of various derivatives thereof (Misawa et al., *J. Bacteriol.*, 172:6704, 1990; Barkcovich et al., *Metab. Eng.*, 3:27, 2001; Wang et al., *Biotechnol. Bioeng.*, 62, 235, 1999).

Using a non-mevalonate pathway starting with the polymerization of glycealdehyde-3-phosphate (hereinafter, referred to as "G3P") and pyruvate (hereinafter, referred to as "PYR") in a metabolic network, lycopene is produced through the synthesis and polymerization of an intermediate, isopentenyl disphosphate (hereinafter, referred to as "IPDP") and the modification of chains.

In the production of IPDP, an ispABCEFGH operon including gene dxs (1-deoxyl-d-xyluose synthase) is involved (Kim et al., *Biotechnol. Bioeng.*, 72:408, 2001). Thus, the introduction of a crt operon absent in *E. coli* made the terminal modification of the $C_{40}$ compound possible, thus making the production of lycopene in *E. coli* possible (Misawa et al., *J. Bacteriol.*, 172:6704, 1990).

Accordingly, to the existing *E. coli* metabolic network model, a crt operon-associated process for the production of lycopene (Alper et al., *Metab. Eng.*, 7:155, 2004) was added to modify and re-construct the existing metabolic network model.

The metabolic network model that produces lycopene was constructed and an FSEOF algorithm was applied thereto, thus screening a new group of gene candidates to be amplified. First, through metabolic flux analysis, the intake rate of an immobilized substrate (glucose) was defined as 10 mmol/gDW/hr, and metabolic fluxes in aerobic conditions were simulated.

As a result, production-associated metabolic flux in a wild-type strain was zero, and the optimum value in a basic strain in which gene dxs producing lycopene has been expressed was 0.0002 mmol/gDW/hr. The above values were calculated by substituting restriction conditions of values experimentally obtained in minimal media. Also, the maximum value of lycopene metabolic flux was 0.62 mmol/gDW/hr. By applying the FSEOF algorithm based on the above-calculated values, genes involved in metabolic fluxes to be amplified could be primarily screened. Table 1 below shows a list of the primarily screened genes involved in the metabolic fluxes to be amplified.

TABLE 1

| | SEOF | 1 | 2 | 3 | 4 | 5 | 6 | 7 |
|---|---|---|---|---|---|---|---|---|
| ProductObjective | ZLyco | 0.0002 | 0.1002 | 0.2002 | 0.3002 | 0.4002 | 0.5002 | 0.6002 |
| Glycolysis | TPI | 8.80403 | 9.14835 | 9.49267 | 9.73338 | 9.81799 | 9.8976 | 9.97721 |
| | FBA | 2.5689 | 2.97335 | 3.37779 | 3.77123 | 4.15445 | 4.53767 | 4.92089 |
| | PFK | 2.5689 | 2.97335 | 3.37779 | 3.77123 | 4.15445 | 4.53767 | 4.92089 |
| | PGI | 8.0451 | 8.82645 | 9.6078 | 9.96642 | 9.97664 | 9.98686 | 9.99708 |
| TCA | CS | 2.01652 | 2.66612 | 3.31572 | 3.85296 | 4.21131 | 4.56966 | 4.928 |
| | ACONT | 2.01652 | 2.66612 | 3.31572 | 3.85296 | 4.21131 | 4.56966 | 4.928 |
| | FUM_rxn | 1.94113 | 2.60234 | 3.26356 | 3.81274 | 4.18332 | 4.55391 | 4.9245 |
| | MDH | 1.95923 | 2.61766 | 3.27609 | 3.8224 | 4.19005 | 4.55769 | 4.92534 |
| | 3UCD1I | 1.71261 | 2.40903 | 3.10546 | 3.63087 | 4.0568 | 4.48273 | 4.90868 |
| | SUCD4 | 1.71261 | 2.40903 | 3.10546 | 3.63087 | 4.0568 | 4.48273 | 4.90868 |
| | SUCOAS | -1.43341 | -2.17286 | -2.9123 | -3.54188 | -3.99489 | -4.4479 | -4.90091 |
| | TEST_AKGD | 1.56147 | 2.28118 | 3.00089 | 3.61019 | 4.04241 | 4.47464 | 4.90686 |
| | ICDHyr | 2.01652 | 2.66612 | 3.31572 | 3.85296 | 4.21131 | 4.56966 | 4.928 |
| Lyc | ZCRTB | 0.0002 | 0.1002 | 0.2002 | 0.3002 | 0.4002 | 0.5002 | 0.6002 |
| | ZCRTE | 0.0004 | 0.2004 | 0.4004 | 0.6004 | 0.8004 | 1.0004 | 1.2004 |
| | ZCRTI | 0.0002 | 0.1002 | 0.2002 | 0.3002 | 0.4002 | 0.5002 | 0.6002 |
| | DMATT | 0.0004 | 0.2004 | 0.4004 | 0.6004 | 0.8004 | 1.0004 | 1.2004 |
| | DXPRIi | 0.0016 | 0.8016 | 1.6016 | 2.4016 | 3.2016 | 4.0016 | 4.8016 |
| | DXPS | 0.0016 | 0.8016 | 1.6016 | 2.4016 | 3.2016 | 4.0016 | 4.8016 |
| | GRTT | 0.0004 | 0.2004 | 0.4004 | 0.6004 | 0.8004 | 1.0004 | 1.2004 |
| | IPDDIi | 0.0004 | 0.2004 | 0.4004 | 0.6004 | 0.8004 | 1.0004 | 1.2004 |
| | IPDPS | 0.0016 | 0.8016 | 1.6016 | 2.4016 | 3.2016 | 4.0016 | 4.8016 |
| | MECDPDH | 0.0016 | 0.8016 | 1.6016 | 2.4016 | 3.2016 | 4.0016 | 4.8016 |
| | MCCDPS | 0.0016 | 0.8016 | 1.6016 | 2.4016 | 3.2016 | 4.0016 | 4.8016 |
| | MEPCT | 0.0016 | 0.8016 | 1.6016 | 2.4016 | 3.2016 | 4.0016 | 4.8016 |
| | CDPMEK | 0.0016 | 0.8016 | 1.6016 | 2.4016 | 3.2016 | 4.0016 | 4.8016 |
| Cofactor | ASAD | -0.12805 | -0.10832 | -0.08859 | -0.12827 | -0.08924 | -0.0502 | -0.01117 |
| | ASPK | 0.12805 | 0.10832 | 0.08859 | 0.12827 | 0.08924 | 0.0502 | 0.01117 |
| | ATPS4r | 57.52936 | 57.64494 | 57.76052 | 57.99994 | 58.36937 | 58.7388 | 59.10824 |
| | CO2t | -20.6676 | -21.365 | -22.0624 | -22.7569 | -23.4488 | -24.1407 | -24.8326 |
| | CYTK1 | 0.06588 | 0.85598 | 1.64607 | 2.43589 | 3.22546 | 4.01502 | 4.80459 |
| | H2Ct | -28.328 | -30.3459 | -32.3638 | -34.346 | -36.2951 | -38.2442 | -40.1933 |
| | HSDy | 0 | 0 | 0 | -0.05995 | -0.04171 | -0.02347 | -0.00522 |
| | HSK | 0 | 0 | 0 | 0.05995 | 0.04171 | 0.02347 | 0.00522 |
| | NDPK3 | 0.07197 | 0.86112 | 1.65028 | 2.43914 | 3.22772 | 4.01629 | 4.80827 |
| | Plt2r | 0.33053 | 0.47967 | 0.6288 | 0.77652 | 0.92293 | 1.06933 | 1.21574 |
| | PPA_rxn | 1.20974 | 2.52381 | 3.83788 | 5.14678 | 6.45088 | 7.75497 | 9.05907 |
| | TEST_NAD1 | 0 | 0 | 0 | 0.63857 | 1.97506 | 3.31156 | 4.64805 |
| | THRS | 0 | 0 | 0 | 0.05995 | 0.04171 | 0.02347 | 0.00522 |

From Table 1, it can be seen that genes associated with the synthesis of G3P and all genes involved in a tricarboxylic pathway were screened. Also, all genes in the non-mevalonate pathway starting with G3P and PYR, and coenzyme-associated genes, were screened.

Figure 3:
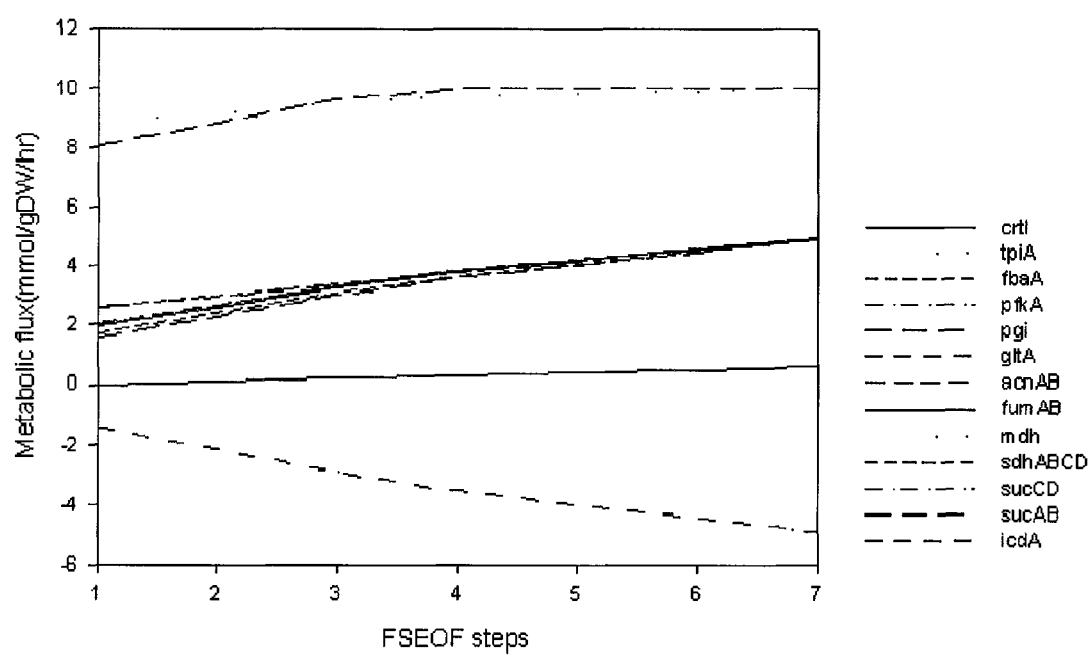
FIG. 3 shows the metabolic flux distribution for genes to be amplified, which is selected using the inventive FSEOF algorithm in order to enhance the production of lycopene.

Then, genes to be amplified were finally screened through the metabolic flux analysis of the primarily screened genes. Among the primarily screened genes, metabolic fluxes showing a tendency to decrease or increase but having an absolute maximum value greater than absolute optimum value only in a few sections were excluded. Based on these values, changes in fluxes for production and genes to be amplified could be comparatively analyzed. FIG. 3 shows metabolic flux distribution in which the genes to be amplified, which is primarily screened by the FSEOF algorithm to enhance the production of lycopene, are involved.

The patterns of the metabolic fluxes screened according to the above-described method showed the form of monotonous increase or decrease. The optimum value of a positive number means a value continuously increasing in the forward direction, and the optimum value of a negative number means a value increasing in the reverse direction. Also, as the positions of reactants and products change from left to right or vise versa, a monotonous decrease in a negative number was shown.

However, since the metabolic fluxes primarily screened through the FSEOF algorithm result from the process of screening sections showing an increase in the change of absolute value, it can be considered that the primarily screened metabolic fluxes are regardless of a positive number or negative number of the optimum value. For this reason, those swung or not started from a value of zero were also screened as metabolic fluxes to be amplified. Accordingly, among these metabolic flux patterns, metabolic fluxes which have not increased in a consistent pattern or which have been changed from a forward direction to a reverse direction or vice versa in the metabolic network were excluded from fluxes to be ultimately amplified.

As a result, pgi, fbaA, tpiA and pfkA were screened as genes to be amplified in a process for improving a producer strain that produces lycopene. Also, among genes having a linear relationship therewith in the non-mevalonate pathway, idi was screened as a gene to be amplified, and among genes in the TCA network, mdh and icdA were screened as genes to be amplified.

In order to examine whether the screened genes to be amplified have any effect on the actual production of lycopene, the screened genes were introduced into E. coli using expression vectors.

To express the screened genes, gene vectors were constructed in the following manner. PCR amplification was performed using wild type E. coli (W3110) as a template with primers shown in Table 2 for the screened genes. Each of the resulting PCR fragments were cleaved with restriction enzymes and introduced into a gene vector.

First, a PCR fragment was obtained using primers of SEQ ID NOS: 1 and 2 and then cleaved with EcoRI and KpnI. The resulting substance was introduced into pTrc99A (Amersham Pharmacia, N.J., USA), thus constructing vector pTD for the amplification of gene dxs.

For gene pgi, a PCR fragment was obtained using primers of SEQ ID NOS: 3 and 4 and then cleaved with XbaI and PstI. The cleaved fragment was introduced into pTD, thus constructing pTDpgi.

For gene pfkA, a PCR fragment was obtained using primers of SEQ ID NOS: 5 and 6 and then cleaved with XbaI and KpnI. The resulting fragment was introduced into pTD, thus constructing pTDpfkA.

For gene fbaA, a PCR fragment was obtained using primers of SEQ ID NOS: 7 and 8 and then cleaved with XbaI and KpnI. The resulting fragment was introduced into pTD, thus constructing pTDfbaA.

For gene tpiA, a PCR fragment was obtained using primers of SEQ ID NOS: 9 and 10 and then cleaved with XbaI and KpnI. The resulting fragment was introduced into pTD, thus constructing pTDtpiA.

For gene icdA, a PCR fragment was obtained using primers of SEQ ID NOS: 11 and 12 and then cleaved with XbaI. The resulting fragment was introduced into pTD, thus constructing pTDicdA.

For gene mdh, a PCR fragment was obtained using primers of SEQ ID NOS: 13 and 14 and then cleaved with XbaII. The resulting fragment was introduced into pTD, thus constructing pTDmdh.

For gene idi, a PCR fragment was obtained using primers of SEQ ID NOS: 15 and 16 and then cleaved with XbaI and KpnI. The resulting fragment was introduced into pTD, thus constructing pTDidi.

For a crtEXYIB operon that produces lycopene, PCR amplification was performed using the genome DNA of Erwinia uredovora (ATCC 19321) as a template with primers of SEQ ID NOS: 17 and 18 shown in Table 2 below. The resulting PCR fragment was cleaved with an EcoRI restriction enzyme and introduced into pACYC184 (Chang et al., J. Bacteriol., 134:1141, 1978), thus constructing gene vector pCar184.

Also, PCR was performed using the above-constructed pCar184 as a template with primers of SEQ ID NOS: 19 and 20 shown in Table 2, and the resulting PCR fragment was cleaved with a DnpI restriction enzyme and subjected to self-fusion, thus constructing pLyc184 including gene crtEIB.

For the production of lycopene, the pLyc184 vector was introduced into E. coli DH5α (New England Lab., MA) by a heat-shock method. The recombinant E. coli strain was added to 50 ml of 2YT medium (16 g/L trypton, 10 g/L yeast extract, 5 g/L sodium chloride) in a 250 ml flask and cultured in a shaking incubator at 30° C. and 200 rpm for 48 hours.

TABLE 2

| | | |
|---|---|---|
| dxs | SEQ ID NO: 1 | 5'-CGGAATTCATGAGTTTTGATATTGC CAAATA |
| | SEQ ID NO: 2 | 5'-GGGGTACC TTATGCCAGCCAGGCCTT GATTT |
| pgi | SEQ ID NO: 3 | 5'-GCTCTAGAGACTGGCGCTACAATCTT CCAAAGTCAC |
| | SEQ ID NO: 4 | 5'-AACTGCAGATGATTAACCGCGCCACG CTTTATAGC |
| pfkA | SEQ ID NO: 5 | 5'-GCTCTAGATGCATTCCAAAGTTCAGA GGTAGTCATG |
| | SEQ ID NO: 6 | 5'-AACTGCAGTCATTAATACAGTTTTTT CGCGCAGTCC |
| fbaA | SEQ ID NO: 7 | 5'-GGGGTACC AGGCC CGACG ATACA GGACA AGA |
| | SEQ ID NO: 8 | 5'-GCTCTAGA TTACA GAACG TCGAT CGCGT TCA |
| tpiA | SEQ ID NO: 9 | 5'-GGGGTACC TTCGC TTATA AGCGT GGAGA ATT |
| | SEQ ID NO: 10 | 5'-GCTCTAGA TTAAG CCTGT TTAGC CGCTT CTG |
| icdA | SEQ ID NO: 11 | 5'-GCTCTAGAAAACCAGTAGCGCTCGA AGGAGAGGTGA |
| | SEQ ID NO: 12 | 5'-GCTCTAGAGCATTACATGTTTTCGA TGATCGCGTCA |
| mdh | SEQ ID NO: 13 | 5'-GCTCTAGAGGCAGCGGAGCAACATA TCTTAGTTTAT |
| | SEQ ID NO: 14 | 5'-GCTCTAGATTACTTATTAACGAACT CTTCGCCCAGG |
| idi | SEQ ID NO: 15 | 5'-GGGGTACCGTGATCAGAATTACATG TGAGAA |
| | SEQ ID NO: 16 | 5'-GCTCTAGATTATTTAAGCTGGGTAA ATGCAG |

TABLE 2-continued

```
crtEXYIB SEQ ID NO: 17 5'-CGGAATTCGGTACCGCACGGTCTGC
                       CAATCCGACG
        SEQ ID NO: 18 5'-CGGAATTCTTTGACCTGATTATCAG
                       CACGGTCGCC
crtEBI  SEQ ID NO: 19 5'-CTTAACTGACGGCAGCGAGTTTT
                       TTG
        SEQ ID NO: 20 5'-GATGAAACCAACTACGGTAATTG
                       GTG
```

The culture broth was centrifuged at 13,000 rpm for 2 minutes, and the cells were collected and suspended in cold acetone. The suspension was maintained in a water bath at 55° C. for 15 minutes to extract lycopene. The extract was subjected to high-performance liquid chromatography to isolate lycopene from the extract, and the lycopene was identified with a UV detector at 470 nm wavelength. The concentration of the sample was calculated by linear interpolation using lycopene with previously known concentration. Table 3 below shows the lycopene concentrations and the lycopene contents resulting from the culture process.

Among the expression vectors in Table 3, the construction of expression vector pAC-LYC04/pTdxs and the culturing of *E. coli* introduced with this vector (Kim et al., *Biotechnol. Bioeng.*, 72:408, 2001), and the construction of expression vector pCW2/pAK32 and the culture of *E. coli* introduced with this vector (Wang et al. *Biotechnol. Prog.*, 16:922, 1999), were performed according to the methods described in the prior literatures.

TABLE 3

| Plasmids | Lycopene conc. (mg L$^{-1}$) | Lycopene content (mg gDCW$^{-1}$) | References |
|---|---|---|---|
| pAC-LYC04/pTdxs | 6.62 | 3.12 | Kim et al., Biotechnol. Bioeng., 72: 408, 2001 |
| pCW2/pAK32 | 0.23 (Astaxanthin) | | Wang et al., Biotechnol. Prog., 16: 922, 1999 |
| pTrc99A/pLyc184 | 2.21 ± 0.03 | 1.29 ± 0.02 | |
| pTD/pLyc184 | 4.95 ± 0.02 | 3.09 ± 0.01 | |
| pTDidi/pLyc184 | 12.85 ± 0.13 | 6.48 ± 0.09 | |
| pTDfbaA/pLyc184 | 6.94 ± 0.73 | 4.62 ± 0.35 | |
| pTDtpiA/pLyc184 | 6.84 ± 0.63 | 4.89 ± 0.34 | |
| pTDpgi/pLyc184 | 5.32 ± 0.26 | 2.73 ± 0.13 | |
| pTDpfkA/pLyc184 | 3.25 ± 0.08 | 1.627 ± 0.04 | |
| pTDicdA/pLyc184 | 4.94 ± 0.23 | 2.98 ± 0.14 | |
| pTDmdh/pLyc184 | 9.06 ± 0.47 | 4.83 ± 0.24 | |

In the test results, in comparison with a control group (pTD/pLyc184), the case where the fbaA gene has been amplified showed a 50% increase in the content of lycopene, and the case where tpiA and mdh genes have been amplified showed a 60% increase in the lycopene content. The case of amplification of the idi gene showed an increase up to 110%. The other screened genes had no great influence on the production of lycopene. This is believed to be because the metabolic network model did not include enzymatic activity and regulatory mechanisms.

In conclusion, among the selected genes, four candidate genes (fbaA, tpiA, mdh and idi) were determined as genes to be amplified, which have a positive effect on an increase in the production of lycopene.

Example 2

Shikimate

Shikimate is a compound of aromatic amino acids and plays as a key precursor for the overproduction of L-phenylalanine, L-tyrosine and tryptophane in *E. coli* or plants. Also, it is a starting material necessary for the synthesis of neuraminidase inhibitor GS4104 (Tamiflu), which is used in the treatment of viral infection.

For shikimate, phosphenolpyruvate (PEP) and erythrose-4-phosphate (E4P) are polymerized with each other to synthesize 3-heptulosonate-7-phosphate (DAHP), from which a shikimate biosynthesis pathway is started. Accordingly, the utilization of E4P and PEP has a great effect on the production of shikimate.

DAHP produces shikimate by aroFGH, aroB, aroD and aroE while consuming single molecular NADPH. Furthermore, shikimate synthesizes common aromatic compounds by aroKL and aroA. It was reported in the prior literature that aroBLA is a reaction-controlling factor, and thus shikimate can be produced using mutants of aroKL from the analysis of accumulated intermediate (Draths et al., *J. Am. Chem. Soc.*, 121:1603, 1999). Also, shikimate could be produced by a strain which has a deletion of aroA to inhibit the production of aromatic compounds (U.S. Pat. No. 6,436,664). These methods adopted gene deletion to produce shikimate.

In this Example, in order to improve a strain that overproduces shikimate, the FSEOF algorithm was applied to screen genes to be amplified.

First, the FSEOF algorithm was performed at the same initial substrate uptake rate and under aerobic conditions as described in Example 1, and the optimum value and maximum value of shikimate metabolic flux to be inputted into an initial algorithm were calculated. As a result, the optimum value and maximum value in a basic strain were 0 mmol/gDW/hr and 7.69289 mmol/gDW/hr, respectively. The FSEOF algorithm was executed based on the optimum value and maximum value, and the results are shown in Table 4 below.

TABLE 4

| | SEOF | 1 | 2 | 3 | 4 | 5 | 6 | 7 | 8 |
|---|---|---|---|---|---|---|---|---|---|
| Shikimate | SKMTRS | 0.000000 | 1.000000 | 2.000000 | 3.000000 | 4.000000 | 5.000000 | 6.000000 | 7.000000 |
| glycolysis | HEXI | 0.000000 | 0.745290 | 1.990400 | 3.235510 | 4.480620 | 5.725730 | 6.370840 | 8.215950 |
| | PGI | 4.964160 | 5.169360 | 5.385240 | 5.601120 | 5.817000 | 6.032880 | 6.248760 | 6.464640 |
| PPP | TKT | 1.294250 | 1.608930 | 1.920300 | 2.231670 | 2.543040 | 2.354410 | 3.165780 | 3.477150 |
| | TALA | 1.270890 | 1.588590 | 1.903000 | 2.217410 | 2.631810 | 2.346220 | 3.160630 | 3.475040 |
| | RPI | −2.626690 | −2.768900 | −2.906950 | −2.045010 | −3.183060 | −3.321120 | −3.459180 | −3.597230 |
| | TKT2 | 0.914750 | 0.278560 | −0.360710 | −0.399980 | −1.639250 | −2.270520 | −2.817790 | −3.557060 |
| Cofactor | DDPA | 0.356120 | 1.310030 | 2.263700 | 3.217380 | 4.171060 | 5.124740 | 6.070420 | 7.032100 |
| | DHOD | 0.356120 | 1.310030 | 2.263700 | 3.217380 | 4.171060 | 5.124740 | 6.070420 | 7.032100 |
| | DHQS | 0.356120 | 1.310030 | 2.363700 | 3.217380 | 4.171060 | 5.124740 | 6.070420 | 7.032100 |

TABLE 4-continued

| SEOF | 1 | 2 | 3 | 4 | 5 | 6 | 7 | 8 |
|---|---|---|---|---|---|---|---|---|
| GLCt2 | 0.000000 | 0.745290 | 1.990400 | 3.235510 | 4.480620 | 5.725730 | 6.970420 | 8.215950 |
| SHK3Or | 0.356120 | 1.310090 | 2.263700 | 3.217380 | 4.171060 | 5.124740 | 6.070420 | 7.032100 |
| FBA | 6.574750 | 6.978380 | 6.878090 | 6.777790 | 6.677490 | 6.577200 | 6.476900 | 6.376600 |
| PFK | 6.574750 | 6.978380 | 6.878090 | 6.777790 | 6.677490 | 6.577200 | 6.476900 | 6.376600 |

Figure 4:
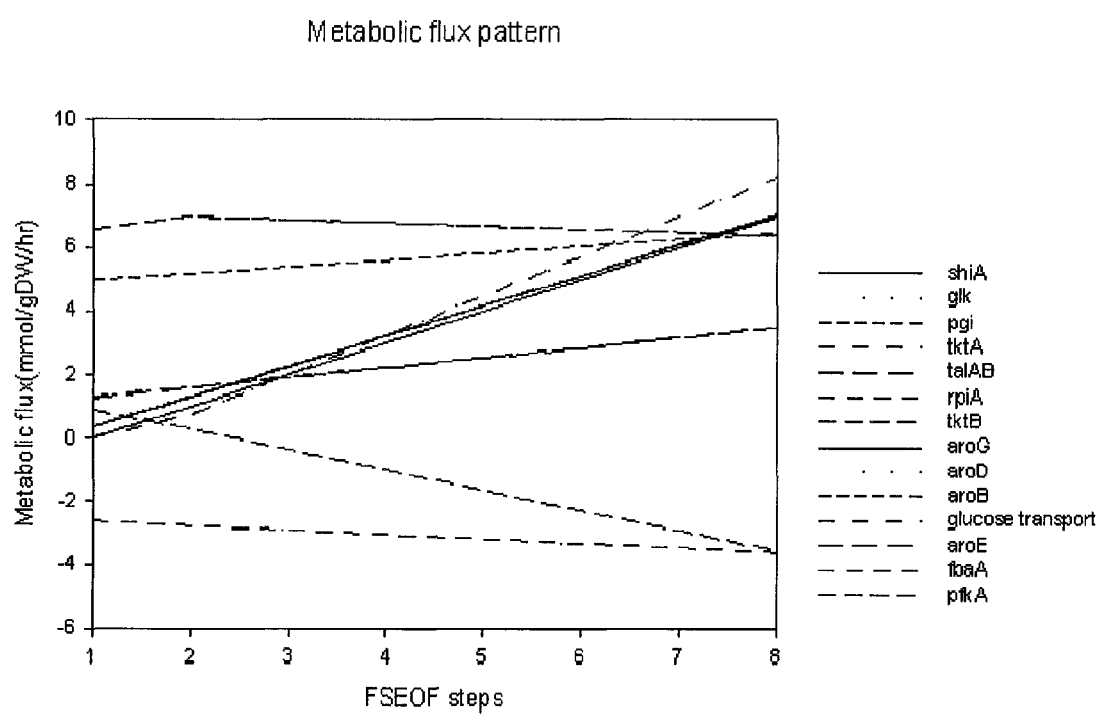
FIG. 4 shows the metabolic flux distribution for genes to be amplified, which is selected using the inventive FSEOF algorithm in order to enhance the production of shikimate.

In the process of interest, pgi, fbaA and pfkA were screened, and in the pentose phosphate pathway, tktA, talAB and rpiA were screened. In the TCA network, any gene was not screened. In addition, aroFGH that directly produces shikimate was also screened. Thus, the metabolic flux pattern of each of the screened genes was analyzed. The patterns of all the screened genes showed monotonous increase. FIG. 4 shows metabolic flux distribution for the genes to be amplified, which are selected through the FSEOF algorithm to enhance the production of shikimate.

Among metabolic flux patterns in which the primarily screened genes are involved, metabolic fluxes whose increasing intervals have not increased in a consistent pattern or which have been changed from the forward direction to the reverse direction or vice versa in the metabolic network were excluded from fluxes to be ultimately amplified. The genes screened in this manner were glk, pgi, tktA, talA, talB and aroG.

To confirm the screening results, various literature reviews were performed. It was reported in the prior literature that, when the tktA of $E.$ $coli$ was amplified and the $E.$ $coli$ strain was cultured using glucose as a substrate, the total amount of quinic acid and dehydroshikimate was then increased from 0.15 mol/mol to 0.24 mol/mol (Knop et al., $J.$ $Am.$ $Chem.$ $Soc.,$ 123:10173, 2001). This result was about 50% of the theoretical yield of shikimate, which is 0.43 mol/mol. The yield of shikimate in said literature was increased from 0.12 mol/mol to 0.18 mol/mol. This suggests that the amplification of tktA is a strategy for increasing the utilization of E4P in the central metabolic network.

As strategy for increasing the utilization of PEP, the inactivation of a phosphotransferase system (PTS) and the amplification of glucose kinase (glk), together with the amplification of tktA, could provide a yield of 0.27 mol/mol (Gibson et al., $Chem.$ $Int.$ $Ed.,$ 40:1945, 2001; Chandran et al., $Biotechnol.$ $Prog.,$ 19:808, 2003). Literature survey could confirm that the amplification of tktA and the amplification of glk can lead to an increase in the production of shikimate.

As described in the prior literature, tktA and glk which can result in an actual increase in production by amplification are genes to be amplified, which are selected through the inventive FSEOF algorithm. Thus, it could be confirmed that the inventive method for screening genes to be amplified are also useful to enhance the production of shikimate.

Example 3

Indigo

Indigo is used as a dye for fibrous material. Indigo is conventionally obtained by extraction from plants or by a chemical synthesis method. With the accumulation of technology by the development of the biological industry, a method for producing indigo using aromatic degradation bacteria was developed (Murdock et al., $Bio/Technol.,$ 11:381, 1993; O'Connor, et al., $Biotechnol.$ $Lett.,$ 20:219, 1998). In addition, a method for producing indigo in an $E.$ $coli$ strain introduced with a gene encoding phenol hydroxylase in $bacillus$ sp. was also developed (U.S. Pat. No. 5,834,297). Also, the production of indigo could be enhanced by developing a new indigo synthesis pathway through the modification of L-tryptophan operon and the enzymatic reaction of naphthalene dioxygenase (NDO) derived from $Pseudomonas$ $putida$ (NDO) and converting L-tryptophan mainly produced in $E.$ $coli$ into indigo (>40 g/L) (Berry et al., $J.$ $Ind.$ $Microbiol.$ $Biotechnol.,$ 28:127, 2002).

Based on the existing central metabolic network playing an important role in the production of L-tryptophan in $E.$ $coli$, genes to be amplified were screened using the FSEOF algorithm.

First, new NDO (naphtalene dioxygenase) was introduced into a constructed $E.$ $coli$ metabolic network model, and the FSEOF algorithm was executed. The FSEOF algorithm was executed at the same initial substrate uptake rate under aerobic conditions as described in Example 1, and the optimum value and maximum value of indigo metabolic flux to be inputted into an initial algorithm were calculated. As a result, the optimum value and maximum value of a basic strain were 0 mmol/gDW/hr and 9.92809 mmol/gDW/hr, respectively.

Through the FSEOF algorithm, the following genes were primarily screened. Namely, in the process of interest, pgi, pfk, fbaA and ppsA were selected as genes to be amplified, and in the pentose phosphate pathway, tktAB, talAB, rpiA and rpe genes were screened. Also, aceB, a gene of the glyoxylate shunt, and acnAB and sucAB genes in the TCA pathway, were screened (Table 5).

TABLE 5

| | SEOF | 1 | 2 | 3 | 4 | 5 | 6 | 7 | 8 | 9 | 10 |
|---|---|---|---|---|---|---|---|---|---|---|---|
| | ND0 | 0 | 1 | 2 | 3 | 4 | 5 | 6 | 7 | 8 | 9 |
| Glycolysis | PGI | 4.96416 | 5.13377 | 5.31406 | 5.43435 | 5.67453 | 5.85492 | 6.03521 | 5.72548 | 8.19759 | 6.6657 |
| | GLCl2 | 0 | 1.16946 | 2.83874 | 4.50601 | 6.17729 | 7.84657 | 9.61585 | 10 | 10 | 10 |
| | HEX1 | 0 | 1.16946 | 2.89974 | 4.50601 | 6.17729 | 7.84657 | 9.61565 | 10 | 10 | 10 |
| | FBA | 6.57475 | 6.76092 | 6.44316 | 6.1254 | 5.80764 | 5.48989 | 5.17212 | 4.75267 | 4.52018 | 4.28768 |
| | PFK | 6.57475 | 6.76092 | 6.44316 | 6.1254 | 5.80764 | 5.48989 | 5.17212 | 4.75267 | 4.52018 | 4.28768 |
| | PP3 | 0 | 0 | 0 | 0 | 0 | 0 | 0 | 0.91703 | 2.91988 | 4.11478 |
| PPF | APE | 2.209 | 1.70845 | 1.20152 | 0.63459 | 0.13764 | −0.3183 | −0.82624 | −0.94503 | −1.95912 | −2.37321 |
| | TKTI | 1.23425 | 1.21538 | 1.2532 | 1.23101 | 1.20883 | 1.18664 | 1.16446 | 1.33595 | 1.20894 | 1.08153 |
| | TALA | 1.28088 | 1.2543 | 1.23442 | 1.21454 | 1.13466 | 1.17478 | 1.1549 | 1.32815 | 1.2042 | 1.01904 |
| | TKT2 | 0.97475 | 0.43308 | −0.06168 | −0.53643 | −1.02118 | −1.50594 | −1.99069 | −2.28088 | −2.86606 | −3.45514 |
| | API | −2.62669 | −2.97723 | −3.32363 | −3.67002 | −4.00641 | −4.36281 | −4.7052 | −5.15787 | −5.42092 | −5.68356 |

TABLE 5-continued

|  | SEOF | 1 | 2 | 3 | 4 | 5 | 6 | 7 | 8 | 9 | 10 |
|---|---|---|---|---|---|---|---|---|---|---|---|
| TCA | MALS | 0.04637 | 0.04183 | 0.03725 | 0.03268 | 0.0281 | 0.02953 | 0.01896 | 0.77061 | 0.50743 | 0.24415 |
|  | ICL | 0 | 0 | 0 | 0 | 0 | 0 | 0 | 0.75632 | 0.49802 | 0.29972 |
| Cofactor&PA | SUCOAS | −3.61208 | −3.61017 | −3.62109 | −3.632 | −3.61292 | −3.65384 | −3.66475 | −2.84512 | −3.28665 | 3.79218 |
|  | ADk1 | 3.33508 | 3.51184 | 3.6825 | 3.85315 | 4.02381 | 4.18447 | 4.36513 | 4.55737 | 6.93503 | 8.91281 |
|  | PPA_rxn | 3.01011 | 3.28753 | 3.48271 | 3.3779 | 3.87308 | 4.06827 | 4.26346 | 4.45234 | 1.6271 | 4.80115 |
|  | GLNS | 1.71854 | 2.06815 | 2.39888 | 2.1252 | 3.06372 | 3.38225 | 3.71077 | 4.03575 | 4.35278 | 4.68981 |
|  | PGOD | 2.01145 | 2.3053 | 2.60789 | 2.91048 | 3.21307 | 3.51566 | 3.81826 | 4.02808 | 4.34779 | 4.66718 |
|  | PSERT | 2.01145 | 2.3053 | 2.60789 | 2.91048 | 3.21307 | 3.51566 | 3.81826 | 4.02808 | 4.34773 | 4.66718 |
|  | PSF_L | 2.01145 | 2.3053 | 2.60789 | 2.91048 | 3.21307 | 3.51566 | 3.81826 | 4.02909 | 4.34773 | 4.66718 |
|  | PRFPS | 0.91648 | 1.26352 | 1.60003 | 2.91048 | 2.51305 | 2.92955 | 3.34607 | 3.76095 | 4.17177 | 4.66718 |
|  | CHDAS | 0.35612 | 0.82122 | 1.2861 | 1.75097 | 2.21585 | 2.58072 | 3.14559 | 3.60974 | 4.07226 | 4.53476 |
|  | DDFA | 0.35612 | 0.82122 | 1.2861 | 1.75097 | 2.21585 | 2.58072 | 3.14559 | 3.60974 | 4.07226 | 4.53476 |
|  | DH0D | 0.35612 | 0.82122 | 1.2861 | 1.75097 | 2.21585 | 2.66072 | 3.14559 | 3.60974 | 4.07226 | 4.53476 |
|  | DH0S | 0.35612 | 0.82122 | 1.2861 | 1.75097 | 2.21585 | 2.66072 | 3.14559 | 3.60974 | 4.07226 | 4.53476 |
|  | P3OVT | 0.35612 | 0.82122 | 1.2861 | 1.75097 | 2.21585 | 2.66072 | 3.14559 | 3.60974 | 4.07226 | 4.53476 |
|  | SHk3Dr | 0.35612 | 0.82122 | 1.2861 | 1.75097 | 2.21595 | 2.66072 | 3.14559 | 3.60974 | 4.07226 | 4.53476 |
|  | SHKK | 0.35612 | 0.82122 | 1.2861 | 1.75097 | 2.21595 | 2.66072 | 3.14559 | 3.60974 | 4.07226 | 4.53476 |
|  | ANFHI | 0.02504 | 0.52259 | 1.02012 | 1.51765 | 2.01518 | 2.51271 | 3.01024 | 3.50772 | 4.00508 | 4.50245 |
|  | ANS | 0.02504 | 0.52259 | 1.02012 | 1.51765 | 2.01518 | 2.51271 | 3.01024 | 3.50772 | 4.00508 | 4.50245 |
|  | PRAII | 0.02504 | 0.52259 | 1.02012 | 1.51765 | 2.01518 | 2.51271 | 3.01024 | 3.50772 | 4.00508 | 4.50245 |
|  | TRFS3 | 0.02504 | 0.52259 | 1.02012 | 1.51765 | 2.01518 | 2.51271 | 3.01024 | 3.50772 | 4.00508 | 4.50245 |
|  | TYFSER | 0.02504 | 0.52259 | 1.02012 | 1.51765 | 2.01518 | 2.51271 | 3.01024 | 3.50772 | 4.00508 | 4.50245 |
|  | TYFCO2 | 0.02504 | 0.52259 | 1.02012 | 1.51765 | 2.01518 | 2.51271 | 3.01024 | 3.50772 | 4.00508 | 4.50245 |
|  | TRPAS2 | −0.02504 | 0.47741 | 1.02012 | 1.43235 | 1.93492 | 2.48723 | 2.99976 | 3.49228 | 3.99492 | 4.49755 |
|  | HSk | 0 | 0 | 0 | 0 | 0 | 0 | 0 | 0.09559 | 0.0584 | 0.02811 |
|  | THFS | 0 | 0 | 0 | 0 | 0 | 0 | 0 | 0.06632 | 0.0584 | 0.02811 |
|  | ANTA2 | 0.01356 | 0.02125 | 0.01892 | 0.3166 | 0.01428 | 0.01195 | 0.00963 | 0.05906 | 0.04367 | 0.02112 |
|  | GSNK | 0 | 0 | 0 | 0 | 0 | 0 | 0 | 0.05906 | 0.03889 | 0.01872 |
|  | NTCe | 0 | 0 | 0 | 0 | 0 | 0 | 0 | 0.05906 | 0.03889 | 0.01872 |
|  | PUNP4 | 0 | 0 | 0 | 0 | 0 | 0 | 0 | 0.05906 | 0.03889 | 0.01872 |
|  | DGX1 | 0 | 0 | 0 | 0 | 0 | 0 | 0 | −0.05906 | −0.03889 | −0.01872 |
|  | NDFK5 | 0 | 0 | 0 | 0 | 0 | 0 | 0 | −0.05906 | −0.03889 | −0.01872 |
|  | PUNP3 | 0 | 0 | 0 | 0 | 0 | 0 | 0 | −0.05906 | −0.03889 | −0.01872 |
|  | HSCy | 0 | 0 | 0 | 0 | 0 | 0 | 0 | −0.08898 | −0.03889 | −0.02871 |
|  | INDOLEIγ | 0 | −1 | −2 | −3 | −4 | −5 | −6 | −7 | −8 | −9 |
|  | H2CI | −41.21385 | −42.01305 | −42.924 | −43.77495 | −45.47685 | −45.3259 | −46.32781 | −47.21701 | −49.19202 | −49.16702 |

Figure 5:
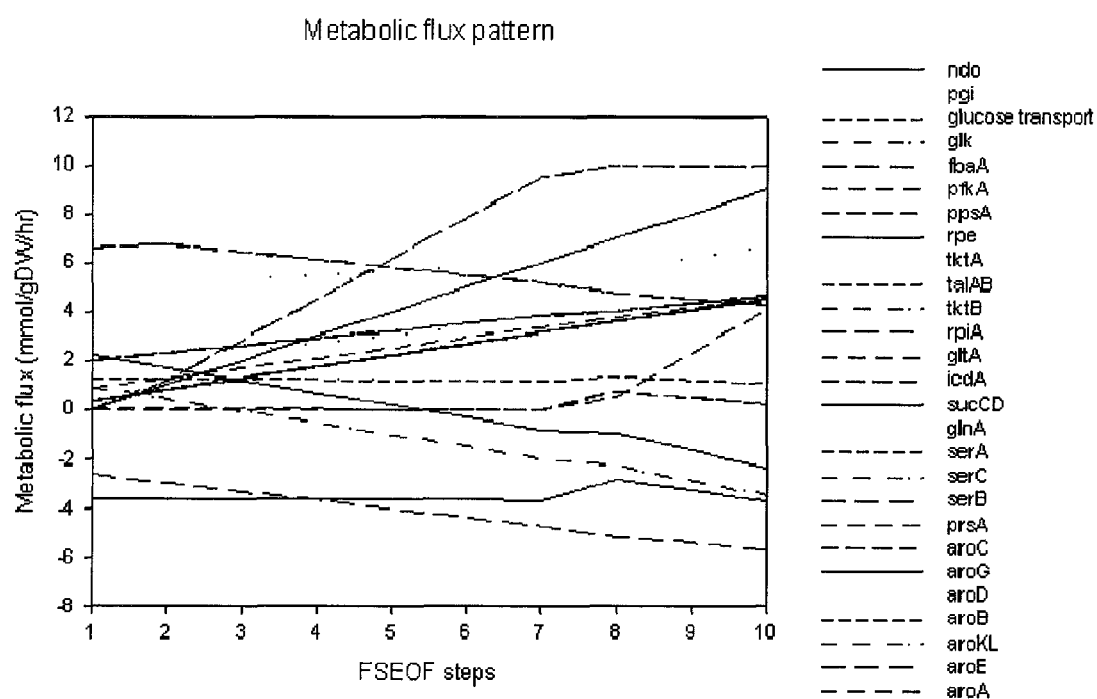
FIG. 5 shows the metabolic flux distribution for genes to be amplified, which is selected using the inventive FSEOF algorithm in order to enhance the production of indigo.

The metabolic flux pattern of each of the screened genes was analyzed. FIG. 5 shows metabolic flux distribution for the genes to be amplified, which are selected through the FSEOF algorithm to enhance the production of indigo. Among these metabolic flux patterns, metabolic fluxes whose increasing intervals have not increased in a consistent pattern were excluded from fluxes to be ultimately amplified. Regarding the production of indigo, sucAB, tktB, pfkA and rpe genes screened through the FSEOF algorithm were excluded from genes to be amplified.

As a result, pgi, glk, fbaA and ppsA in the process of interest, tktA and rpiA in the pentose phosphate pathway, and aceB in the TCA network, could be finally screened as genes to be amplified.

Next, literatures describing an increase in the production of indigo resulting from metabolic engineering approaches were surveyed. In aromatic production such as an indigo production pathway, the following strategies were introduced in order to increase a change in carbon flux.

Namely, it was reported that the deletion of gene pykFA and the amplification of tktA in a strain having the phosphotransferase system (PTS) could lead to 3 and 1.5-fold increases in carbon metabolic flux, respectively, and the amplification of tktA in a mutant strain having a deletion of PTS could lead to a 5.8 fold increase in carbon metabolic flux, and the introduction of glk gene together with the amplification of tktA could result in about 20 fold increase in carbon metabolic flux (Gosset et al., *J. Ind. Microbiol.*, 17:47, 1996).

This is believed to result from an increase in the utilization of PEP (phosphoenolpyruvate) and E4P (D-erythrose 4-phosphate) substrates of DAHP synthase (3-deoxy-D-arabio hetulosonate 7-phosphate synthase) in the first step of the indigo production pathway. Therefore, the amplification of tktA to increase the utilization of E4P and the deletion of the pykFA gene to increase the utilization of PEP in the production of indigo by metabolic engineering methods could be suggested. Also, a metabolic engineering approach having carbon flux increased, together with introducing aroG$^{fbr}$ which stops the inhibition of aroG feedback could provide an increase of 30% in the production of indigo (Berry et al., *J. Ind. Microbiol. Biotechnol.*, 28:127, 2002).

The results in the prior literatures as described above coincided with the results of amplification of genes selected through the gene screening method according to the present invention. The tktA gene and the glk gene were directly selected as genes to be amplified, and an increase in a pathway starting with gene aroG was screened. Also, the ppsA gene which can directly increase the substrate utilization of the gene PEP, could also be screened. Accordingly, the genes screened according to the inventive method coincided with the results shown in the prior literatures, indicating that the utility thereof was verified.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

As described in detail above, according to the present invention, an organism producing a useful substance can be effectively improved by a method comprising: selecting metabolic fluxes to be amplified and genes involved in the metabolic fluxes in the range between the optimum value of useful substance production-associated metabolic flux and the maximum flux value corresponding to the theoretical maximum yield of the useful substance when the value of cell growth-associated metabolic flux is the maximum under the condition where fermentation data are applied or not applied in the host organism for producing useful substance whose genom-scale metabolic network model is constructed; and introducing and/or amplifying the selected genes in the host organism.

---

What is claimed is:

1. A method for identifying genes for enhancing the production of a target useful substance, the method comprising the steps of:
   (a) providing a metabolic network model specific to the production of the target useful substance in said host microorganism, wherein the target useful substance is selected from the group consisting of lycopene, shikimate, and indigo;
   (b) calculating a maximum value of metabolic flux associated with production of the target useful substance by the host microorganism in the provided metabolic network model, comprising executing the following algorithm to determine said maximum value:

$$\sum_{j=1}^{M} S_{ij} v_j = 0 \quad \forall\, i \in M,\, \forall\, j \in N$$
$$v_j^\alpha \le v_j \le v_j^\beta \qquad v_j \in i$$

wherein: $S_{ij}$ is the reaction coefficient matrix of the provided metabolic network model, and $v_j$ is metabolic flux;
   (c) calculating an optimum value of metabolic flux associated with production of the target useful substance by the host microorganism in the provided metabolic network model when the growth of the microorganism is maximum, comprising executing the following algorithm to determine said optimum value:

$$\sum_{j=1}^{} S_{ij} v_j = 0 \quad \forall\, i \in M,\, \forall\, j \in N$$
$$v_j^\alpha \le v_j \le v_j^\beta \qquad v_j \in i$$

wherein: $S_{ij}$ is the reaction coefficient matrix of the provided metabolic network model, and $v_j$ is metabolic flux;
   (d) executing a flux scanning based on enforced objective flux (FSEOF) algorithm on a suitably programmed computer, for the maximum value of metabolic flux associated with production of the target useful substance by the host microorganism in the provided metabolic network model, as calculated in step (b), and the optimum value of metabolic flux associated with production of the target useful substance by the host microorganism in the provided metabolic network model, as calculated in step (c), wherein the FSEOF algorithm selects metabolic fluxes whose absolute value increases in a range between the optimum value calculated in step (c) and the maximum value calculated in step (b), and wherein the FSEOF algorithm is represented as follows:

$$f_{p,j} = f_{p,opt} + \frac{y_k}{n}(f_{p,max} - f_{p,opt})$$

$$\left[\begin{array}{l} \sum_{j=1}^{M} S_{ij} v_j = 0 \quad \forall\, i \in M,\, \forall\, j \in N \\ v_j^\alpha \le v_j \le v_j^\beta \qquad v_j \in \mathbb{R} \end{array}\right]$$

$$Y = \{y_k \in \mathcal{C} \mid y_k = 0, 1 \ldots, n\}$$

if $|v_j|_{max} > |v_{opt}|$, $v_j$ is selected, wherein $S_{ij}$ is the reaction coefficient matrix of the provided metabolic network model, $v_j$ is metabolic flux, $v_{opt}$ is the optimum value of metabolic flux, $|v_j|_{max}$ is the absolute maximum value of metabolic flux, calculated by the FSEOF algorithm, $f_{p,j}$ is production-associated metabolic flux, $f_{p,max}$ is the maximum value corresponding to the theoretical maximum yield of production-associated metabolic flux, $f_{p,opt}$ is the optimum value of production-associated metabolic flux of the target useful substance, Y is a set including the characteristic factor of the FSEOF algorithm, and $y_k$ is the characteristic factor of the FSEOF algorithm in the set Y;
   (e) identifying genes that are involved in the metabolic fluxes that have been selected by the FSEOF algorithm in step (d);
   (f) selecting an optimal set of genes for enhancing the production of the target useful substance which are involved in metabolic fluxes showing a monotonous increase from the genes identified in step (e); and
   (g) preparing the target useful substance, comprising culturing an organism that has been improved by said optimal set of genes for production of said target useful substance.

2. A method for improving a microorganism producing a target useful substance the method comprising the steps of:
   (a) providing a metabolic network model specific to the production of the target useful substance in said host microorganism, wherein the target useful substance is selected from the group consisting of lycopene, shikimate, and indigo;
   (b) calculating a maximum value of metabolic flux associated with production of the target useful substance by the microorganism in the provided metabolic network model, comprising executing the following algorithm to determine said maximum value:

$$\sum_{j=1}^{M} S_{ij} v_j = 0 \quad \forall\, i \in M,\, \forall\, j \in N$$
$$v_j^\alpha \le v_j \le v_j^\beta \qquad v_j \in i$$

wherein: $S_{ij}$ is the reaction coefficient matrix of the provided metabolic network model, and $v_j$ is metabolic flux;

(c) calculating an optimum value of metabolic flux associated with production of the target useful substance by the host microorganism in the provided metabolic network model when the growth of the microorganism is maximum, comprising executing the following algorithm to determine said optimum value:

$$\sum_{j=1} S_{ij} v_j = 0 \quad \forall\, i \in M,\, \forall\, j \in N$$

$$v_j^\alpha \le v_j \le v_j^\beta \qquad v_j \in i$$

wherein: $S_{ij}$ is the reaction coefficient matrix of the provided metabolic network model, and $v_j$ is metabolic flux;

(d) executing a flux scanning based on enforced objective flux (FSEOF) algorithm on a suitably programmed computer, for the maximum value of metabolic flux associated with production of the target useful substance by the host microorganism in the provided metabolic network model, as calculated in step (b), and the optimum value of metabolic flux associated with production of the target useful substance by the host microorganism in the provided metabolic network model, as calculated in step (c), wherein the FSEOF algorithm selects metabolic fluxes whose absolute value increases in a range between the optimum value calculated in step (c) and the maximum value calculated in step (b), and wherein the FSEOF algorithm is represented as follows:

$$f_{p,j} = f_{p,opt} + \frac{y_k}{n}(f_{p,\max} - f_{p,opt})$$

$$\begin{bmatrix} \sum_{j=1}^{M} S_{ij} v_j = 0 & \forall\, i \in M,\, \forall\, j \in N \\ v_j^\alpha \le v_j \le v_j^\beta & v_j \in i \end{bmatrix}$$

$$Y = \{y_k \in \mathcal{C} \mid y_k = 0, 1 \ldots, n\}$$

if $|v_j|_{max} > |v_{opt}|$, $v_j$ is selected, wherein $S_{ij}$ is the reaction coefficient matrix of the provided metabolic network model, $v_j$ is metabolic flux, $v_{opt}$ is the optimum value of metabolic flux, $|v_j|_{max}$ is the absolute maximum value of metabolic flux, calculated by the FSEOF algorithm, $f_{p,j}$ is production-associated metabolic flux, $f_{p,max}$ is the maximum value corresponding to the theoretical maximum yield of production-associated metabolic flux, $f_{p,opt}$ is the optimum value of production-associated metabolic flux of the target useful substance, Y is a set including the characteristic factor of the FSEOF algorithm, and $y_k$ is the characteristic factor of the FSEOF algorithm in the set Y;

(e) identifying genes that are involved in the metabolic fluxes that have been selected by the FSEOF algorithm in step (d);

(f) selecting from the identified genes of step (e) those genes involved in metabolic fluxes showing a form of a continuous increase as genes to be amplified for improvement of the microorganism;

(g) constructing a mutant of the microorganism with improved production of the target useful substance by introducing the genes to be amplified into the microorganism and/or amplifying said genes in the microorganism; and (h) culturing the mutant organism constructed in the step (g) and producing the target useful substance.

3. The method of claim 2, wherein the useful substance is lycopene and the genes to be amplified for producing lycopene are selected from the group consisting of fbaA, tpiA, mdh and idi.

4. The method of claim 2, wherein the useful substance is shikimate and the genes to be amplified for producing shikimate are selected from the group consisting of glk, pgi, tktA, talA, talB and aroG.

5. The method of claim 2, wherein the useful substance is indigo and the genes to be amplified for producing indigo are selected from the group consisting of pgi, glk, fbaA, ppsA, tktA, rpiA and aceB.

* * * * *

UNITED STATES PATENT AND TRADEMARK OFFICE
CERTIFICATE OF CORRECTION

PATENT NO. : 8,977,530 B2  Page 1 of 1
APPLICATION NO. : 11/722709
DATED : March 10, 2015
INVENTOR(S) : Sang Yup Lee et al.

It is certified that error appears in the above-identified patent and that said Letters Patent is hereby corrected as shown below:

In the specification,

Column 7, line 39: "arc" should be -- are --.

Column 19, Sequence Listing, SEQ ID NO 20: "<223> OTHER INFORMATION: primer" should be -- "<223> OTHER INFORMATION: primer for pTD --.

Signed and Sealed this
Twelfth Day of May, 2015

Michelle K. Lee
*Director of the United States Patent and Trademark Office*

SEQUENCE LISTING

```
<160> NUMBER OF SEQ ID NOS: 20

<210> SEQ ID NO 1
<211> LENGTH: 31
<212> TYPE: DNA
<213> ORGANISM: Artificial
<220> FEATURE:
<223> OTHER INFORMATION: primer

<400> SEQUENCE: 1
cggaattcat gagttttgat attgccaaat a                              31

<210> SEQ ID NO 2
<211> LENGTH: 31
<212> TYPE: DNA
<213> ORGANISM: Artificial
<220> FEATURE:
<223> OTHER INFORMATION: Primer for pTD

<400> SEQUENCE: 2
ggggtacctt atgccagcca ggccttgatt t                              31

<210> SEQ ID NO 3
<211> LENGTH: 36
<212> TYPE: DNA
<213> ORGANISM: Artificial
<220> FEATURE:
<223> OTHER INFORMATION: Primer for pTDpgi

<400> SEQUENCE: 3
gctctagaga ctggcgctac aatcttccaa agtcac                         36

<210> SEQ ID NO 4
<211> LENGTH: 35
<212> TYPE: DNA
<213> ORGANISM: Artificial
<220> FEATURE:
<223> OTHER INFORMATION: Primer for pTDpgi

<400> SEQUENCE: 4
aactgcagat gattaaccgc gccacgcttt atagc                          35

<210> SEQ ID NO 5
<211> LENGTH: 36
<212> TYPE: DNA
<213> ORGANISM: Artificial
<220> FEATURE:
<223> OTHER INFORMATION: Primer for pTDpfkA

<400> SEQUENCE: 5
gctctagatg cattccaaag ttcagaggta gtcatg                         36

<210> SEQ ID NO 6
<211> LENGTH: 36
<212> TYPE: DNA
<213> ORGANISM: Artificial
<220> FEATURE:
<223> OTHER INFORMATION: Primer for pTDpfkA

<400> SEQUENCE: 6
```

```
aactgcagtc attaatacag tttttttcgcg cagtcc                        36
```

<210> SEQ ID NO 7
<211> LENGTH: 31
<212> TYPE: DNA
<213> ORGANISM: Artificial
<220> FEATURE:
<223> OTHER INFORMATION: Pirmer for pTDfbaA

<400> SEQUENCE: 7

```
ggggtaccag gcccgacgat acaggacaag a                              31
```

<210> SEQ ID NO 8
<211> LENGTH: 31
<212> TYPE: DNA
<213> ORGANISM: Artificial
<220> FEATURE:
<223> OTHER INFORMATION: Primer for pTDfbaA

<400> SEQUENCE: 8

```
gctctagatt acagaacgtc gatcgcgttc a                              31
```

<210> SEQ ID NO 9
<211> LENGTH: 31
<212> TYPE: DNA
<213> ORGANISM: Artificial
<220> FEATURE:
<223> OTHER INFORMATION: Primer for pTDtpiA

<400> SEQUENCE: 9

```
ggggtaccct cgcttataag cgtggagaat t                              31
```

<210> SEQ ID NO 10
<211> LENGTH: 31
<212> TYPE: DNA
<213> ORGANISM: Artificial
<220> FEATURE:
<223> OTHER INFORMATION: Primer for pTDtpiA

<400> SEQUENCE: 10

```
gctctagatt aagcctgttt agccgcttct g                              31
```

<210> SEQ ID NO 11
<211> LENGTH: 36
<212> TYPE: DNA
<213> ORGANISM: Artificial
<220> FEATURE:
<223> OTHER INFORMATION: Primer for pTDicdA

<400> SEQUENCE: 11

```
gctctagaaa accagtagcg ctcgaaggag aggtga                         36
```

<210> SEQ ID NO 12
<211> LENGTH: 36
<212> TYPE: DNA
<213> ORGANISM: Artificial
<220> FEATURE:
<223> OTHER INFORMATION: Primer for pTDicdA

<400> SEQUENCE: 12

```
gctctagagc attacatgtt ttcgatgatc gcgtca                         36
```

<210> SEQ ID NO 13
<211> LENGTH: 36
<212> TYPE: DNA

```
<213> ORGANISM: Artificial
<220> FEATURE:
<223> OTHER INFORMATION: Primer for pTDmdh

<400> SEQUENCE: 13
gctctagagg cagcggagca acatatctta gtttat                              36

<210> SEQ ID NO 14
<211> LENGTH: 36
<212> TYPE: DNA
<213> ORGANISM: Artificial
<220> FEATURE:
<223> OTHER INFORMATION: Primer for pTDmdh

<400> SEQUENCE: 14
gctctagatt acttattaac gaactcttcg cccagg                              36

<210> SEQ ID NO 15
<211> LENGTH: 31
<212> TYPE: DNA
<213> ORGANISM: Artificial
<220> FEATURE:
<223> OTHER INFORMATION: primer for pTDidi

<400> SEQUENCE: 15
ggggtaccgt gatcagaatt acatgtgaga a                                   31

<210> SEQ ID NO 16
<211> LENGTH: 31
<212> TYPE: DNA
<213> ORGANISM: Artificial
<220> FEATURE:
<223> OTHER INFORMATION: Primer for pTDidi

<400> SEQUENCE: 16
gctctagatt atttaagctg ggtaaatgca g                                   31

<210> SEQ ID NO 17
<211> LENGTH: 35
<212> TYPE: DNA
<213> ORGANISM: Artificial
<220> FEATURE:
<223> OTHER INFORMATION: Primer for pCar184

<400> SEQUENCE: 17
cggaattcgg taccgcacgg tctgccaatc cgacg                               35

<210> SEQ ID NO 18
<211> LENGTH: 35
<212> TYPE: DNA
<213> ORGANISM: Artificial
<220> FEATURE:
<223> OTHER INFORMATION: Primer for pCar184

<400> SEQUENCE: 18
cggaattctt tgacctgatt atcagcacgg tcgcc                               35

<210> SEQ ID NO 19
<211> LENGTH: 26
<212> TYPE: DNA
<213> ORGANISM: Artificial
<220> FEATURE:
<223> OTHER INFORMATION: Primer for pLyc184

<400> SEQUENCE: 19
cttaactgac ggcagcgagt tttttg                                         26
```

```
<210> SEQ ID NO 20
<211> LENGTH: 26
<212> TYPE: DNA
<213> ORGANISM: Artificial
<220> FEATURE:
<223> OTHER INFORMATION: Primer for pLyc184

<400> SEQUENCE: 20
gatgaaacca actacggtaa ttggtg                                          26
```